US006709845B1

(12) United States Patent
Pollock (10) Patent No.: US 6,709,845 B1
(45) Date of Patent: Mar. 23, 2004

(54) PRODUCTION OF MODIFIED POLYSACCHARIDE S-7

(75) Inventor: Thomas J. Pollock, San Diego, CA (US)

(73) Assignees: Shin-Etsu Bio, Inc., San Diego, CA (US); Shin-Etsu Chemical Co., Ltd, Tokyo (JP)

( * ) Notice: Subject to any disclaimer, the term of this patent is extended or adjusted under 35 U.S.C. 154(b) by 157 days.

(21) Appl. No.: 09/607,248

(22) Filed: Jun. 30, 2000

Related U.S. Application Data (60) Provisional application No. 60/142,121, filed on Jul. 2, 1999.

(51) Int. Cl.⁷ .............................................. C12D 13/04
(52) U.S. Cl. ....................................... 435/101; 536/123
(58) Field of Search ............................ 536/123; 435/101

(56) References Cited

U.S. PATENT DOCUMENTS

| | | | |
|---|---|---|---|
| 3,894,976 A | 7/1975 | Kang et al. ............ 200/17.4 ST |
| 3,915,800 A | * 10/1975 | Kang et al. |
| 3,960,832 A | * 6/1976 | Kang et al. |
| 3,979,303 A | 9/1976 | Kang et al. ............... 252/8.5 C |
| 4,462,836 A | 7/1984 | Baker et al. ................... 106/92 |
| 5,114,846 A | 5/1992 | Inoue et al. ................... 435/34 |
| 5,137,825 A | 8/1992 | Inoue et al. ................. 435/245 |
| 5,156,961 A | 10/1992 | Inoue et al. ................. 435/124 |
| 5,177,018 A | 1/1993 | Inoue et al. ............. 435/253.5 |
| 5,190,866 A | 3/1993 | Inoue et al. ................. 435/119 |
| 5,194,386 A | 3/1993 | Pollock et al. ........... 435/252.3 |
| 5,208,153 A | 5/1993 | Inoue et al. ................. 435/119 |
| 5,210,033 A | 5/1993 | Inoue et al. ............. 435/172.1 |
| 5,258,291 A | 11/1993 | Inoue et al. ................. 435/119 |
| 5,266,484 A | 11/1993 | Inoue et al. ............. 435/253.5 |
| 5,268,460 A | 12/1993 | Thorne et al. .............. 536/1.11 |
| 5,279,961 A | 1/1994 | Pollock et al. ........... 435/252.3 |
| 5,310,677 A | 5/1994 | Pollock et al. ........... 435/252.1 |
| 5,338,841 A | 8/1994 | Pollock et al. ............. 536/23.7 |
| 5,340,743 A | 8/1994 | Pollock et al. ........... 435/252.3 |
| 5,342,773 A | 8/1994 | Thorne et al. ............... 435/200 |
| 5,354,671 A | 10/1994 | Pollock ....................... 435/101 |
| 5,401,659 A | 3/1995 | Thorne et al. ............ 435/252.5 |
| 5,434,078 A | 7/1995 | Pollock et al. ........... 435/253.6 |
| 5,472,870 A | 12/1995 | Pollock et al. ........... 435/252.1 |
| 5,493,015 A | 2/1996 | Murofushi et al. ......... 536/127 |
| 5,580,763 A | 12/1996 | Honma et al. ............... 435/104 |
| 5,595,892 A | 1/1997 | Murofushi et al. ......... 435/104 |
| 5,602,241 A | 2/1997 | Maruyama et al. ......... 536/127 |
| 5,679,556 A | 10/1997 | Homma et al. ............. 435/104 |
| 5,702,927 A | 12/1997 | Murofushi et al. ......... 435/104 |
| 5,705,368 A | 1/1998 | Murofushi et al. ......... 435/104 |
| 5,709,801 A | 1/1998 | Murofushi et al. ......... 210/770 |
| 5,772,912 A | 6/1998 | Lockyer et al. ............... 252/70 |
| 5,854,034 A | 12/1998 | Pollock et al. ............. 435/101 |
| 5,864,034 A | 1/1999 | Murofushi et al. ......... 536/124 |
| 5,912,151 A | 6/1999 | Pollock et al. ............. 435/104 |
| 5,972,695 A | 10/1999 | Murofushi et al. ....... 435/289.1 |
| 5,985,623 A | 11/1999 | Pollock et al. ............. 435/101 |
| 5,994,107 A | 11/1999 | Murofushi et al. ......... 435/104 |
| 6,010,899 A | 1/2000 | Thorne et al. ............ 435/254.1 |
| 6,027,925 A | 2/2000 | Pollock et al. ............. 435/104 |
| 6,030,817 A | 2/2000 | Pollock et al. ............. 435/104 |
| 6,110,731 A | 8/2000 | Murofushi et al. ....... 435/283.1 |
| 6,194,564 B1 | 2/2001 | Murofushi et al. ......... 536/144 |
| 6,387,666 B1 | 5/2002 | Thorne et al. .............. 435/102 |

FOREIGN PATENT DOCUMENTS

| | | |
|---|---|---|
| CA | 2089837 C | 7/1999 |
| EP | 0 287 363 B1 | 9/1994 |
| EP | 0 624 651 B1 | 11/2001 |

OTHER PUBLICATIONS

Falk et al., "Structural studies of the exocellular polysaccharide from *Sphingomonas paucimobilis* strain I–886," *Carbohydrate Research* 285:67–79, 1996.

Gulin et al., "Structural studies of S–7, another exocellular polysaccharide containing 2–deoxy–arabino–hexuronic acid," *Carbohydrate Research* 331:285–290, 2001.

Hebbar et al., "Characterization of exopolysaccharides produced by rhizobacteria," *Appl. Microbiol. Biotechnol.* 38:248–253, 1992.

Pollock et al., "Assignment of Biochemical Functions to Glycosyl Transferase Genes Which Are Essential for Biosynthesis of Exopolysaccharides in Sphingomonas Strain S88 and *Rhizobium leguminosarum*," *J Bacteriol.* 180(3):586–593, Feb. 1998.

Pollock T.J., "Gellan–related polysaccharides and the genus Sphingomonas," *Journal of General Microbiology* 139:1939–1945, 1993.

* cited by examiner

*Primary Examiner*—Leon B. Lankford, Jr.
(74) *Attorney, Agent, or Firm*—Seed Intellectual Property Law Group PLLC (57) ABSTRACT

A modified S7 polysaccharide is disclosed. The polysaccharide contains 20% less glucose that S7. An S7c6 gene cluster is disclosed. A mutated Sphingomonas is also disclosed.

3 Claims, 4 Drawing Sheets

FIG. 1

```
1                                                50
AAGCTTAATGCGGGCACTGCCTAGCTTGCGGGTGCCGGCTCCATCGGGAG
GCGGCGCTTGTAGGAGTGCGTTCGGCATGGCGTCCGATCTCGTTGCGGAG
CCCGATCCGGCGGCCACCATCCTCTGGGTGGGGCAGGACCGGGAAGGGCA
TTGGCTGGTCCAGGAAAATCACGGTCTGATGGAGGGTCGCTTCGTGTCGC
GCGCGGCGGCGTGGCAGTTCGCGCGGGCTGAGCGGCACGGCTTTCCCGGT
GCCAAATGCGCCGAGGCGGGGCAGCCGCTGGTGCCGTGCATCTCCTTCGC
GCCGGTCGCCGCCGACGAGCGCGCACCGCGCTGCGCGGCCTGAGGAGACG
GCCATGCAGCTTGCCTATGCCTATGCCGTGCCGCCGGTGCGATCCGGCGC
CCAGCTTTCCGCCATCGTTCGCCATGCGCTGTGCGATGCCGCAGAGGCCG
TCGCCGCGCGCGATCTCCGCTGGCCGGCGGTGCTCGATCAGCTAAAGATG
CTGCGGGCGGCGGGGCGGCGGAGCGTCCGCATCGTCGATGCCGCGTGCGG
TAACGGCGCGCTGTTGCTGCCGACACTGAGGCAGGCCCGCGCGCTCGGCT
TCGTCGCGATCGAAGCGCGGGGGGTGGACGGCGATGCCGCGGCGCTCGCC
CGTGCCCGCCGCGCGGCGGCGGCGATGGCGGATCTCGCCATCGCGGTGCA
GTTTGATTGCGGCACCGTCGAAGCGGCGCTGCGCGCAGAGGCCGCCTTTC
CTGCCGATATCCTGCTCTACGCCGCGGACCGAACGGAGATGGCGCGTTTC
GCCGCGCTCGCACGCCGTGCCGGGGACATGGCGCTGGGCGGTCCACGCCG
GGAGTCGGGAGAATGAGCCGCCAAGGCGACCGCTTCTGGCGTGGCGTGGG
TGCCTTTCTGTTGATCGCCGGCGGCTTGGCGGGGACGCTGACCGATATCA
GCGGGCCGGAAGGGGCGGGGACGCTGCTGCTGCTCGGCTTCCCGCTCGCG
ATCCTCGGCCTCGTGCTGGTGGTGCAGGGCAAGCGCGCGCCGCTGGCGAT
CCGCGTCGAGTGCAGCCGCCATCGGCACCTGCCCGAGCGCCTGCAG
                                              1096
```

FIG. 2

```
1                                                  50
CTGCAGCCGAAGAAGAAGGCCCCTGCCGCGCCGCCGCCCCGGCTGGGCGA
GAGCGAGGCGCGCGCGATCCTCGGCGTCGACGACGCGGCGGGTCCCGACG
AGATCCGTGCGGCGCACCGCAGGCTCGTCTCGGCGCTGCACCCGGACCGC
GGCGGCTCGGCCGAGCTTACCCGGCGGATCAATCTGGCCCGCGATACGTT
GCTGCGCGGCTGAGGTCCGTCCTCTTCACGTAACATTTGCCTGCAACGAT
GTTGCAGTGCAAAATATTAATCTTTCTATGTCTCGCGCGTCTTGAAACTT
CGTTTCGAGTCGCGGAAGAGGCGCGCATCTTTACCTTCGGGAGGGCTTAC
```

```
351
ATGACGCACCGTTTCGATCCTACGTCGCTGCGCGAATACGACATCCGCGG
AATCGTGGGGAAGACGCTGGGTCCGGACGACGCGCGTGCGATCGGCCGTG
GCTTCGCGACGCTGCTGCGCCGCGCCGGCGGCCGCCGGGTGGCGGTGGGC
CGCGACGGCCGCATTTCCTCGCCGATGCTCGAGGCCGCGCTGATCGAGGG
CCTGACCGCTTCGGGCTGCGACGTGGTGCGCACCGGCATGGGCCCGACGC
CGATGCTATATTATGCCGAGGCAACGCTGGAGGTGGATGGCGGCATCCAG
ATTACCGGCAGCCATAATCCCGGCAACTACAATGGCTTCAAGATGGTGTT
CCAGCACCGCTCGTTCTTCGGCCAGGACATCCAGACGCTGGGCAAGATGG
CGGCGGAAGGCGATTGGGACGAAGGCGACGGCACCGAGACGGTGACCGAC
GCGGACATCGAGGACCTCTATGTCAGCCGCCTGATCGCGGGCTACGCCGG
CGGTTCGTACAAGATCGGCTGGGACGCGGGCAACGGCGCCGCCGGCCCGG
TGATCGAGAAGCTCGTCAAGCTGCTGCCGGGTGAGCACCATACGCTGTTC
ACCGATGTGGACGGTAATTTCCCCAACCATCATCCCGATCCTACCGAAGA
GAAGAATCTCGCCGATCTGAAGAAGCTCGTCGCCGAGAAGAACCTCGATT
TCGGTCTCGCTTTCGACGGCGACGGCGATCGTCTGGGCGCGATCGACGGC
CAGGGCCGGGTGGTGTGGGGCGACCAGCTGCTCTCGATCCTCGCCGAGCC
GGTGCTGCGCGTCGATCCGGGCGCGACGATCATCGCCGACGTCAAGGCCA
GCCAGGCGCTGTACGACCGGATCGCCGAGCTCGGCGGCAAGCCGGTGATG
TGGAAGACCGGCCACAGCCTGATCAAGACCAAGATGAAGGAAACCGGCGC
CCCGCTCGCGGGCGAGATGAGCGGCCACATCTTCTTCGCGCAGGACTATT
ACGGCTTCGACGACGCCCAGTACGCCGCGATCCGCCTGATCCAGGCGGTG
CACGTGATCGGCAAGTCGCTCACCCAGCTCAAGGACGAGATGCCGGCGAT
GGTCAACACGCCGGAGATGCGCTTCCAGGTCGACGAAAGCCGCAAGTTCC
CGGTCGTCGAGGAAGTGCTCGACCGGCTGGAAGCCGACGGCGCCCAGGTC
GACCGTACCGACGGTGCGCGGGTCAACACCGATGACGGCTGGTGGCTGCT
GCGCGCATCCAACACCCAAGACGTGCTCGTTGCGCGTGCCGAGGCGAAGG
ACCAGGCGGGTCTTGATCGCCTGATGGCGCAGATCGACGACCAGCTCGGC
AAGAGCGGCATCGTCCGCGGCGAGCAGGCGGCGCATTGA
                                     1736
                                           1750
                                     GCTGCTTTCCC
TCTCCCCCTCAGGGAGAGGGAGCGACTGACGTGGACGTTTGGGGGAGGCT
CTCGAAGCCTTCCCCCCGTCATCCTCGCGAAGGCGGGGATCC
                                     1842
```

FIG. 3

```
1                                                50
MTHRFDPTSLREYDIRGIVGKTLGPDDARAIGRGFATLLRRAGGRRVAVG
RDGRISSPMLEAALIEGLTASGCDVVRTGMGPTPMLYYAEATLEVDGGIQ
ITGSHNPGNYNGFKMVFQHRSFFGQDIQTLGKMAAEGDWDEGDGTETVTD
ADIEDLYVSRLIAGYAGGSYKIGWDAGNGAAGPVIEKLVKLLPGEHHTLF
TDVDGNFPNHHPDPTEEKNLADLKKLVAEKNLDFGLAFDGDGDRLGAIDG
QGRVVWGDQLLSILAEPVLRVDPGATIIADVKASQALYDRIAELGGKPVM
WKTGHSLIKTKMKETGAPLAGEMSGHIFFAQDYYGFDDAQYAAIRLIQAV
HVIGKSLTQLKDEMPAMVNTPEMRFQVDESRKFPVVEEVLDRLEADGAQV
DRTDGARVNTDDGWWLLRASNTQDVLVARAEAKDQAGLDRLMAQIDDQLG
KSGIVRGEQAAH
           462
```

*FIG. 4*

PRODUCTION OF MODIFIED POLYSACCHARIDE S-7

CROSS REFERENCE TO RELATED APPLICATIONS

This application is a regular patent application of U.S. patent application Ser. No. 60/142,121, filed on Jul. 2, 1999 now abandoned.

BACKGROUND LITERATURE

Polysaccharide S-7 (abbreviated S-7) is the subject of four expired patents: (1) U.S. Pat. No. 3,960,832 issued to Kelco Jun. 1, 1976 and comprising a single composition of matter claim; (2) U.S. Pat. No. 3,915,800 issued to Kelco on Oct. 28, 1975 and comprising the growth of a naturally occurring bacterial strain *Azotobacter indicus* (deposited as ATCC 21423) in a submerged aerated culture in a nutrient medium and recovering the polysaccharide; (3) U.S. Pat. No. 3,894,976 issued on Jul. 15, 1975 and claiming use of S-7 in water based paints; and (4) U.S. Pat. No. 3,979,303 issued Sep. 7, 1976 and claiming use of S-7 in oil well drilling. A recent US patent (U.S. Pat. No. 5,772,912) issued Jun. 30, 1998 claims use of S-7 in anti-icing formulations, and another (U.S. Pat. No. 4,462,836) issued Jul. 31, 1984 claims use of S-7 in cement. The published literature concerning this polysaccharide is limited to a 1977 review by the Kelco inventors that is based on the information in their published patents, and two brief studies by others concerning conditions for growing the naturally occurring bacterium. The parent bacterium is referred to here as Sphingomonas strain S7 since it was reassigned to a new genus (T. J. Pollock, 1993, Journal of General Microbiology, volume 139, pages 1939–1945).

SUMMARY OF THE INVENTION

First, modified derivatives of the naturally occurring parental bacterium Sphingomonas strain S7 were constructed by genetic engineering that exhibit increased conversion of the carbon source in a nutrient culture medium into the product exopolysaccharide S-7, compared to the unmodified parent strain.

Second, a polysaccharide was prepared from one of the genetically-modified derivatives that has a carbohydrate composition which is different from the parent polysaccharide S-7, and which confers increased viscosity on the polymer while in the fermentation broth or after isolation of the polymer.

At this time we do not know the chemical structure of the derived polysaccharide, so we do not know the basis for the change in physical properties.

UTILITY

Polysaccharides like S7 are used to modify the viscosity of aqueous solutions. Several polymers have this capacity, such as xanthan gum, cellulose, and guar. A new polymer like that produced by Sphingomonas strain S7/pRK-S7c6, which is described below and which represents a new composition of matter, shows increased viscosity at lower concentrations.

EXAMPLE 1 (CULTURE CONDITIONS)

The culture medium for Sphingomonas strain S7 and the derivatives includes the following components dissolved in 1 liter of tap water: 20 g glucose, 1 g ammonium nitrate, 0.5 g soluble soy protein, 3.2 g dipotassium phosphate, 1.6 g monopotassium phosphate, 0.2 g magnesium sulfate, and 0.1% v/v of concentrated trace minerals. The concentrated trace minerals were dissolved in deionized water at the following final concentrations: 10 mM $FeCl_3$, 10 mM $ZnCl_2$, 10 mM $MnCl_2$, 1 mM $CoCl_2$, 1 mM $Na_2MoO_4$, and 1 mM $CuSO_4$. For solid medium agar was added to 1.5% w/v before sterilization by autoclaving at 121° C. for 20 min. Bacteria cultured on agar plates were incubated at 30° C. for 2–4 days. For culture volumes of 10–500 ml, bacteria were grown in liquid medium at 30° C. in baffled Erlenmeyer flasks with rotary shaking at 160 rpm. All culture volumes were not more than one-half of the maximum flask capacity.

Seed cultures for the fermentations were prepared in two stages. First a single representative colony was inoculated into 100 ml of liquid medium containing selective antibiotics as required and grown for 18 hours until mid to late exponential phase, and then dispensed into 2 ml aliquots in plastic tubes and frozen at −70° C. Second, to prepare a 5% v/v seed culture for a 4L fermentation, one frozen tube was thawed and a portion, usually 0.5–1.5 ml, was inoculated into 250 ml of medium and shaken for 18 hours. After this period the seed cultures usually achieved an optical density at 600 nm of 3–6, with a final pH of 5.5–6.5.

Fermentations were carried out in 3–4 L of medium using New Brunswick BioFlo III and 3000 equipment. The round bottomed vessel had a marine impeller at the top pushing downward, and two equally spaced 6-bladed Rushton impellers at the midpoint and at the bottom of the shaft. No baffles were present on the periphery of the vessel. Agitation was initially 50 rpm and was under the control of the dissolved oxygen sensor which was set to a minimum of 20–30%. Agitation increased as the culture became dense to a maximum of 1000 rpm. Air was supplied at I volume per minute. The culture pH was initially adjusted to 7. During the exponential phase of growth it decreased naturally to about 6.0–6.2, and then after the ammonium was depleted the pH increased to around 6.5–6.8, and then decreased slowly to the end of the cycle to around 5.8–6.2. Control of pH with additions of KOH or HCl was not necessary. Small amounts of antifoam (1–5 ml, Sigma 204) were added as needed during the exponential phase of growth. As the culture viscosity increased above 10,000 cp (Brookfield LVTDV-II, spindle 4, 12 rpm, 25° C.) the dissolved oxygen usually decreased to zero, the temperature, which was initially set to 30.0° C., began to fluctuate by 0.3° C., and as much as one-half of the broth volume, the portion furthest from the impellers, remained stationary. For each fermentation an automatic record was kept of temperature, dissolved oxygen, pH, and agitation. Measurements were made of absorbance at 600 nm, ammonium concentration, residual glucose concentration, viscosity, and dry weight of the biomass precipitated with two volumes of isopropylalcohol.

EXAMPLE 2 (GENETIC MODIFICATIONS)

Preparation of a library of S7 genes. Strain S7 was cultured in 5 ml of YM medium by shaking at 30° C. After adding 0.55 ml of 10×TE (100 mM Tris-HCl, 10 mM EDTA, pH 8), 0.3 ml of 10% sodium dodecylsulfate, and 0.03 ml of 20 mg/ml proteinase K, the cultures were incubated with shaking for one hour at 65° C. After adding 1 ml of 5M NaCl and 0.8 ml of 10% CTAB (hexadecyltrimethylammoniumbromide) in 1M NaCl the lysates were incubated 30 min at 65° C., and then extracted once with chloroform and once with phenol:chloroform (1:1). The upper aqueous phase was removed and added to 0.6 volumes of isopropylalcohol and then dried. The precipitate was resuspended with a mixture of 0.6 ml of 1×TE containing 0.7 M NaCl and 0.1 ml of 10% CTAB in 1M NaCl, incubated 30 min at 65° C., extracted once with chloroform, and then precipitated with two volumes of ethanol. After drying the pellet was resuspended in 0.1 ml of 1×TE. High molecular weight DNA was partially digested with SalI enzyme. The SalI-digested S7 DNA was treated with Kienow DNA polymerase to add dCMP and dTMP to the cohesive ends (35), heated for 20 min at 70° C. and then precipitated with ethanol. The vector plasmid pRK311 was digested with BamHI enzyme, purified by phenol extraction and ethanol precipitation, treated with Kienow DNA polymerase to add dGMP and dAMP (35), and purified. Equal molar amounts of vector and insert fragments were ligated (T4 DNA ligase), packaged into bacteriophage λ (Gigapack IIXL; Stratagene), and transfected into *Escherichia coli* DH5α. One library of 1,700 and one of 3,400 tetracycline-resistant (Tetr) colonies were separately pooled and frozen. The Tet$^r$ colonies (10 of 10 tested) contained inserts of 25 to 30 kbp with internal SalI restriction sites.

Figure 1:
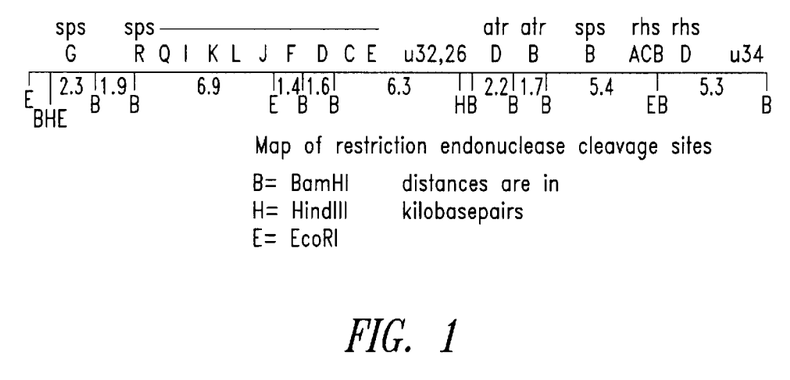

Isolation of the S7c6 gene cluster. Cells representing the entire pooled library were mixed with cells of an exopolysaccharide-negative mutant (such as S88m265) of a related strain S88, such that each recipient bacterium received a different plasmid member of the library. The mating procedures are routine and described in T. J. Pollock el al. 1998 Journal of Bacteriology volume 180 pages 586–593. Alternatively, one can routinely enrich for eps-negative mutants of strain S7 or other Sphingomonas strains on agar plates containing YM and a growth-inhibiting concentration of bacitracin, for example 0.1–10 mg/ml. Among the surviving bacitracin-resistant mutants of the parent strain will be a significant minority of eps-negative colonies which are recognizable because the colonies are translucent and watery compared to the opaque and rubbery eps+ parents. A small number of potential eps-negative isolates may be tested in shake flasks for absence of eps production, in other words for the absence of viscosity in the broth and of isopropylalcohol-precipitable material. After the bacterial mating with the library, a few of the hundreds of recipient colonies that became Tetr also exhibited synthesis of an exopolysaccharide as was evident by inspecting the colony appearances. Restoration of polysaccharide synthesis in the mutant by one of the cloned DNA's from the library caused that colony to be more opaque and rubbery in surface texture. The plasmids from several of the exopolysaccharide-positive colonies were isolated and analyzed for the specific pattern of cleavage by restriction endonucleases, and several unique segments of cloned DNA were recognized. One of these was clone S7c6 and it was compared to a previously cloned DNA segment from strain S88 for which the entire DNA sequence is known by DNA-DNA hybridization. The S7c6 clone contains gene sequences partially homologous to the spsGSRQKLJFDCE-BrhsACBD cluster of genes from strain S88. A map of sites of cleavage for restriction endonucleases is given in FIG. 1. A subclone of this cluster was prepared by digestion with restriction enzymes and contains only the spsBrhsACBD segment, which is abbreviated Brhs. Separately, the pRK311-S7c6 and the pRK311-spsBrhsACBD plasmids were transferred by conjugation into the parental strain S7 for analysis of exopolysaccharide production.

Figure 2:
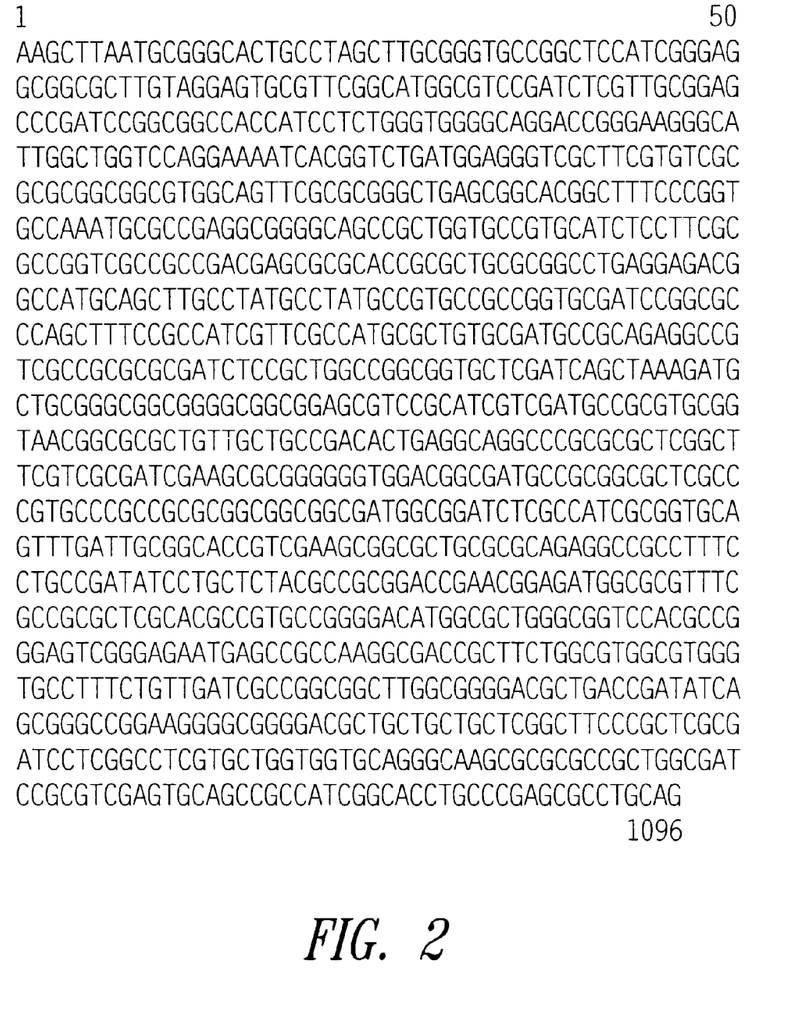

A segment of 1096 base pairs corresponding to the rightmost portion of the central 6.3 kbp BamHI-HindIII segment was sequenced. The DNA sequence is given in FIG. 2. The sequence allows the construction of DNA-specific hybridization probes to screen libraries of segments from the chromosomal DNA. Thus one does not need to use complementation of eps-negative mutants for the cloning of this S7 region.

Figure 4:
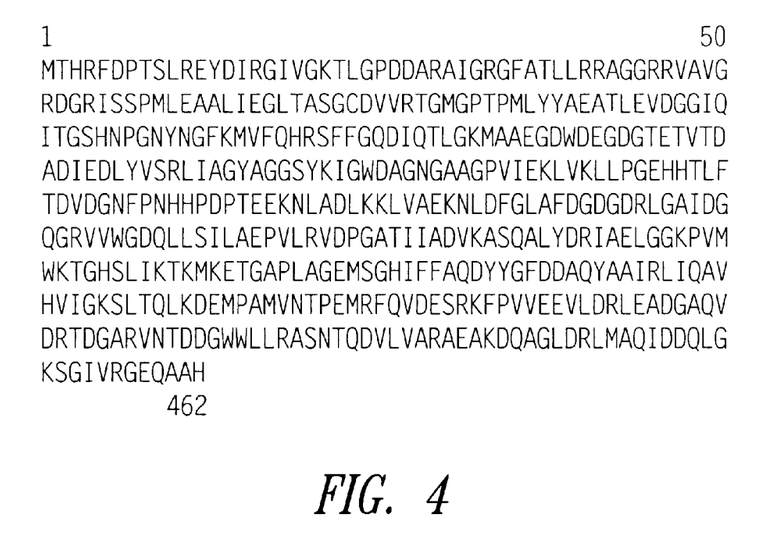

Isolation of the phosphoglucomutase gene. A mutant of *Escherichia coli* (GSC5527) deficient in phosphoglucomutase was obtained from the *E. coli* Genetic Stock Center (New Haven, Conn.), and used as a recipient for the entire S7 gene library. Of the hundreds of bacteria which received a plasmid a few were restored to Pgm$^+$. The Pgm$^+$ exconjugants were observed as large white colonies on M63+ galactose agar plates after over layering the colonies with iodine in dilute agar, while the parental Pgm$^-$ mutants give black colonies. The screening method was described by Adhya and Schwartz, 1971, J. Bacteriol., volume 108, page 621. The overlapping cloned pgm segments indicated that the region in common contained the pgm gene and this segment was cloned into the plasmid vector pRK311 and also into a small vector for DNA sequencing. The DNA sequence was determined and it showed considerable homology to other pgm genes isolated from other bacterial genera, eukaryotic microorganisms, plants and animals. The homology between the amino acid sequence of the Sphingomonas S7 pgm gene and the sequence of the Sphingomonas S60 gene (reference: Applied and Environmental Microbiology Volume 66, pages 2252–2258, 2000) is so extensive that both are expected to behave similarly when inserted into the Sphingomonas. Other related pgm genes are expected to also behave similarly in the context of our invention. The DNA sequence is given in FIG. 3 where the bases which code for the amino acids of the PGM protein are between bases numbered 351 through 1736. The deduced amino acid sequence is given in FIG. 4. Thepgm gene was also cloned together with the spsBrhsACBD genes onto plasmid pRK311. Separately the pRK311-pgm and pRK311-pgm-spsBrhsACBDplasmids, abbreviated as pRK-pgm and pRK-pgmBrhs, were transferred by conjugation into the parental strain S7 for analysis of exopolysaccharide production.

EXMAMPLE 3 (CONVERSION YIELDS)

The results of fermentations with unmodified and genetically modified derivatives of Sphingomonas strain S7 are given in Table 1. Each of the modified strains converts a higher proportion of glucose into the product exopolysaccharide S-7. This indicates that multiple copies of genes isolated from the S7c6 sps gene cluster or of the pgm gene improve the productivity of strain S7. Either the entire S7c6 gene cluster can be used or a smaller segment including the spsB and rhsACBD genes.

TABLE 1

| Plasmid in strain S7 | Absorbance 600 nm | Viscosity cp | S-7 EPS (g/l) | Residual glucose (g) | Conversion yield (g EPS/g glucose) |
|---|---|---|---|---|---|
| none | 10.6 | 22500 | 16.5 | 0 | 52 |
| pRK-S7c6 | 7.8 | 30600 | 17.2 | 3 | 59 |
| pRK-Brhs | 9.3 | 20400 | 16.0 | 5 | 58 |
| pRK-pgm | 11.4 | 20900 | 16.0 | 3 | 55 |
| pRK-pgmBrhs | 9.1 | 23700 | 17.1 | 2 | 57 |

EXAMPLE 4 (NEW COMPOSITION)

As shown in Table 1, the broth viscosity for strain S7 carrying additional copies of the plasmid pRK-S7c6 was increased compared to that of unmodified strain S7. After purification of the exopolysaccharide from the broth, the EPS S7c6 retained its high viscosity as indicated in Table 2. EPS S7c6 is the exopolysaccharide produced by the Sphingomonas strain S7 carrying plasmid pRK-S7c6. The increased viscosity per gram of purified EPS suggested a new composition for the S7c6 polymer. The carbohydrate compositions for each of the exopolysaccharides from S7 and the genetically modified derivatives were determined following acid hydrolysis. The ratio of glucose to rhamnose is given in Table 2. The S7c6 EPS has a unique sugar composition with relatively less glucose residues. Table 2 shows that the new composition is linked to the high viscosity.

The carbohydrate compositions were determined for samples of the culture broths after precipitation of the EPS with 2 volumes of isopropylalcohol. About 8–10 mg of dried material were hydrolyzed in 0.25 ml 2M trifluoroacetic acid at 100° C. for 4.5 hours, and then dried in a vacuum. The dry residue was resuspended in 0.05 ml of deionized water, dried again in a vacuum and finally resuspended in 0.2 ml pure water. The hydrolysate was passed through a spin filter and then 7.5 microliters were diluted with 493 microliters of pure water, and 10 microliters were applied to the chromatography column.

TABLE 2

| Source | Viscosity[1] (cp) | Carbohydrate composition[2] (glc:rha) |
|---|---|---|
| S7 unmodified | 2770 | 5.4 |
| S7 with pRK-S7c6 | 3810 | 4.2 |
| S7 with pRK-Brhs | 2270 | 5.6 |
| S7 with pRK-pgm | 2860 | 5.3 |

[1]Measured with a Brookfield LVTDV-II viscometer with spindle 4 at 12 rpm and at 25° C.
[2]Given as the ratios of the peak areas on HPLC chromatograms for glucose and rhamnose.

Deposits

The following two bacterial strains were deposited with the Patent Depository at the American Type Culture Collection at 10801 University Boulevard, Manassas, Va. 20110, on Jun. 29, 2000 pursuant to the Budapest Treaty for the International Recognition of the Deposit of Microrganisms:
Sphingomonas strain S7 with plasmid pRK311-S7c6, also denoted as S7/pRK-S7c6; and
Sphingomonas strain S7 with plasmid pRK311-pgm spsB rhsACBD, also denoted as S7/pRK-pgmBrhs.

I claim:

1. A polysaccharide produced by aerobically fermenting a Sphingomonas bacterium in a nutrient aqueous broth for a time sufficient to produce a fermentation broth comprising a modified S7 polysaccharide having at least 20% less glucose compared to polysaccharide S7, wherein the bacterium contains an S7c6 gene cluster or segment thereof, said segment including at least an spsB gene and an rhsACBD gene cluster.

2. A fermentation broth comprising a modified S7 polysaccharide having at least 20% less glucose compared to polysaccharide S7, wherein the modified S7 polysaccharide is produced by a Sphingomonas bacterium containing an S7c6 gene cluster or segment thereof, said segment including at least an spsB gene and an rhsACBD gene cluster.

3. A fermentation broth produced by aerobically fermenting a Sphingomonas bacterium in a nutrient aqueous broth for a time sufficient to produce a fermentation broth comprising a modified S7 polysaccharide having at least 20% less glucose compared to polysaccharide S7, wherein the bacterium contains an S7c6 gene cluster or segment thereof, said segment including at least an spsB gene and an rhsACBD gene cluster.

* * * * *

SEQUENCE LISTING

<160> NUMBER OF SEQ ID NOS: 3

<210> SEQ ID NO 1
<211> LENGTH: 1096
<212> TYPE: DNA
<213> ORGANISM: Sphingomonas sp.

<400> SEQUENCE: 1

```
aagcttaatg cgggcactgc ctagcttgcg ggtgccggct ccatcgggag gcggcgcttg      60
taggagtgcg ttcggcatgg cgtccgatct cgttgcggag cccgatccgg cggccaccat     120
cctctgggtg gggcaggacc gggaagggca ttggctggtc caggaaaatc acggtctgat     180
ggagggtcgc ttcgtgtcgc gcgcggcggc gtggcagttc gcgcgggctg agcggcacgg     240
ctttcccggt gccaaatgcg ccgaggcggg gcagccgctg gtgccgtgca tctccttcgc     300
gccggtcgcc gccgacgagc gcgcaccgcg ctgcgcggcc tgaggagacg gccatgcagc     360
ttgcctatgc ctatgccgtg ccgccggtgc gatccggcgc ccagctttcc gccatcgttc     420
gccatgcgct gtgcgatgcc gcagaggccg tcgccgcgcg cgatctccgc tggccggcgg     480
tgctcgatca gctaaagatg ctgcgggcgg cggggcggcg gagcgtccgc atcgtcgatg     540
ccgcgtgcgg taacggcgcg ctgttgctgc cgacactgag gcaggcccgc gcgctcggct     600
tcgtcgcgat cgaagcgcgg ggggtggacg gcgatgccgc ggcgctcgcc cgtgcccgcc     660
gcgcggcggc ggcgatggcg gatctcgcca tcgcggtgca gtttgattgc ggcaccgtcg     720
aagcggcgct gcgcgcagag gccgcctttc ctgccgatat cctgctctac gccgcggacc     780
gaacggagat ggcgcgtttc gccgcgctcg cacgccgtgc cggggacatg gcgctgggcg     840
```

-continued

```
gtccacgccg ggagtcggga gaatgagccg ccaaggcgac cgcttctggc gtggcgtggg      900
tgcctttctg ttgatcgccg gcggcttggc ggggacgctg accgatatca gcgggccgga      960
aggggcggga acgctgctgc tgctcggctt cccgctcgcg atcctcggcc tcgtgctggt     1020
ggtgcagggc aagcgcgcgc cgctggcgat ccgcgtcgag tgcagccgcc atcggcacct     1080
gcccgagcgc ctgcag                                                     1096
```

<210> SEQ ID NO 2
<211> LENGTH: 1842
<212> TYPE: DNA
<213> ORGANISM: Sphingomonas sp.

<400> SEQUENCE: 2

```
ctgcagccga agaagaaggc ccctgccgcg ccgccgcccc ggctgggcga gagcgaggcg       60
cgcgcgatcc tcggcgtcga cgacgcggcg ggtcccgacg agatccgtgc ggcgcaccgc      120
aggctcgtct cggcgctgca cccggaccgc ggcggctcgg ccgagcttac ccggcggatc      180
aatctggccc gcgatacgtt gctgcgcggc tgaggtccgt cctcttcacg taacatttgc      240
ctgcaacgat gttgcagtgc aaaatattaa tctttctatg tctcgcgcgt cttgaaactt      300
cgtttcgagt cgcggaagag gcgcgcatct ttaccttcgg gagggcttac atgacgcacc      360
gtttcgatcc tacgtcgctg cgcgaatacg acatccgcgg aatcgtgggg aagacgctgg      420
gtccggacga cgcgcgtgcg atcggccgtg gcttcgcgac gctgctgcgc cgcgccggcg      480 ccgccgggt ggcggtgggc cgcgacgcc gcatttcctc gccgatgctc gaggccgcgc       540
tgatcgaggg cctgaccgct cgggctgcga cgtggtgcg caccggcatg ggcccgacgc      600
cgatgctata ttatgccgag caacgctgg aggtggatgg cggcatccag attaccggca      660
gccataatcc cggcaactac aatggcttca agatggtgtt ccagcaccgc tcgttcttcg      720
gccaggacat ccagacgctg ggcaagatgg cggcggaagg cgattgggac gaaggcgacg      780
gcaccgagac ggtgaccgac gcggacatcg aggacctcta tgtcagccgc ctgatcgcgg      840
gctacgccgg cggttcgtac aagatcggct gggacgcggg caacgcgcc gccggcccgg      900 tgatcgagaa gctcgtcaag ctgctgccgg gtgagcacca tacgctgttc accgatgtgg      960
acggtaattt ccccaaccat catcccgatc ctaccgaaga aagaatctc gccgatctga     1020 agaagctcgt cgccgagaag aacctcgatt tcggtctcgc tttcgacggc gacggcgatc     1080
gtctgggcgc gatcgacggc cagggccggg tggtgtgggg cgaccagctg ctctcgatcc     1140
tcgccgagcc ggtgctgcgc gtcgatccgg gcgcgacgat catcgccgac gtcaaggcca     1200
gccaggcgct gtacgaccgg atcgccgagc tcggcggcaa gccggtgatg tggaagaccg     1260
gccacagcct gatcaagacc aagatgaagg aaaccggcgc cccgctcgcg ggcgagatga     1320
gcggccacat cttcttcgcg caggactatt acggcttcga cgacgcccag tacgccgcga     1380
tccgcctgat ccaggcggtg cacgtgatcg gcaagtcgct cacccagctc aaggacgaga     1440
tgccggcgat ggtcaacacg ccggagatgc gcttccaggt cgacgaaagc cgcaagttcc     1500
cggtcgtcga ggaagtgctc gaccggctgg aagccgacgg cgcccaggtc gaccgtaccg     1560
acggtgcgcg ggtcaacacc gatgacggct ggtggctgct cgcgcatcc aacacccaag     1620 acgtgctcgt tgcgcgtgcc gaggcgaagg accaggcggg tcttgatcgc ctgatggcgc     1680
agatcgacga ccagctcggc aagagcggca tcgtccgcgg cgagcaggcg gcgcattgag     1740
ctgctttccc tctccccctc aggagagggg agcgactgac gtggacgttt gggggaggct     1800
ctcgaagcct tcccccgtc atcctcgcga aggcggggat cc                        1842
```

-continued

```
<210> SEQ ID NO 3
<211> LENGTH: 462
<212> TYPE: PRT
<213> ORGANISM: Sphingomonas sp.

<400> SEQUENCE: 3

Met Thr His Arg Phe Asp Pro Thr Ser Leu Arg Glu Tyr Asp Ile Arg
1               5                   10                  15

Gly Ile Val Gly Lys Thr Leu Gly Pro Asp Asp Ala Arg Ala Ile Gly
            20                  25                  30

Arg Gly Phe Ala Thr Leu Leu Arg Arg Ala Gly Gly Arg Arg Val Ala
        35                  40                  45

Val Gly Arg Asp Gly Arg Ile Ser Ser Pro Met Leu Glu Ala Ala Leu
    50                  55                  60

Ile Glu Gly Leu Thr Ala Ser Gly Cys Asp Val Val Arg Thr Gly Met
65                  70                  75                  80

Gly Pro Thr Pro Met Leu Tyr Tyr Ala Glu Ala Thr Leu Glu Val Asp
                85                  90                  95

Gly Gly Ile Gln Ile Thr Gly Ser His Asn Pro Gly Asn Tyr Asn Gly
            100                 105                 110

Phe Lys Met Val Phe Gln His Arg Ser Phe Phe Gly Gln Asp Ile Gln
        115                 120                 125

Thr Leu Gly Lys Met Ala Ala Glu Gly Asp Trp Asp Glu Gly Asp Gly
    130                 135                 140

Thr Glu Thr Val Thr Asp Ala Asp Ile Glu Asp Leu Tyr Val Ser Arg
145                 150                 155                 160

Leu Ile Ala Gly Tyr Ala Gly Gly Ser Tyr Lys Ile Gly Trp Asp Ala
                165                 170                 175

Gly Asn Gly Ala Ala Gly Pro Val Ile Glu Lys Leu Val Lys Leu Leu
            180                 185                 190

Pro Gly Glu His His Thr Leu Phe Thr Asp Val Asp Gly Asn Phe Pro
        195                 200                 205

Asn His His Pro Asp Pro Thr Glu Glu Lys Asn Leu Ala Asp Leu Lys
    210                 215                 220

Lys Leu Val Ala Glu Lys Asn Leu Asp Phe Gly Leu Ala Phe Asp Gly
225                 230                 235                 240

Asp Gly Asp Arg Leu Gly Ala Ile Asp Gly Gln Gly Arg Val Val Trp
                245                 250                 255

Gly Asp Gln Leu Leu Ser Ile Leu Ala Glu Pro Val Leu Arg Val Asp
            260                 265                 270

Pro Gly Ala Thr Ile Ile Ala Asp Val Lys Ala Ser Gln Ala Leu Tyr
        275                 280                 285

Asp Arg Ile Ala Glu Leu Gly Gly Lys Pro Val Met Trp Lys Thr Gly
    290                 295                 300

His Ser Leu Ile Lys Thr Lys Met Lys Glu Thr Gly Ala Pro Leu Ala
305                 310                 315                 320

Gly Glu Met Ser Gly His Ile Phe Phe Ala Gln Asp Tyr Tyr Gly Phe
                325                 330                 335

Asp Asp Ala Gln Tyr Ala Ala Ile Arg Leu Ile Gln Ala Val His Val
            340                 345                 350

Ile Gly Lys Ser Leu Thr Gln Leu Lys Asp Glu Met Pro Ala Met Val
        355                 360                 365

Asn Thr Pro Glu Met Arg Phe Gln Val Asp Glu Ser Arg Lys Phe Pro
    370                 375                 380
```

-continued

```
Val Val Glu Glu Val Leu Asp Arg Leu Glu Ala Asp Gly Ala Gln Val
385                 390                 395                 400

Asp Arg Thr Asp Gly Ala Arg Val Asn Thr Asp Asp Gly Trp Trp Leu
                405                 410                 415

Leu Arg Ala Ser Asn Thr Gln Asp Val Leu Val Ala Arg Ala Glu Ala
                420                 425                 430

Lys Asp Gln Ala Gly Leu Asp Arg Leu Met Ala Gln Ile Asp Asp Gln
            435                 440                 445

Leu Gly Lys Ser Gly Ile Val Arg Gly Glu Gln Ala Ala His
        450                 455                 460
```